United States Patent [19]

Clark, Jr. et al.

[11] Patent Number: 4,933,172

[45] Date of Patent: Jun. 12, 1990

[54] METHOD OF AND COMPOSITIONS FOR TREATING DESTRUCTIVE PERIODONTAL DISEASE

[75] Inventors: Joseph D. Clark, Jr., Randolph; Ivan T. Myers, Bernardsville, both of N.J.; Kenneth S. Kornman; Stanley C. Holt, both of San Antonio, Tex.

[73] Assignee: Warner-Lambert Co., Morris Plains, N.J.

[21] Appl. No.: 254,526

[22] Filed: Oct. 6, 1988

[51] Int. Cl.$^5$ .............................................. A61K 7/16
[52] U.S. Cl. ..................................... 424/49; 514/900; 514/901; 514/902
[58] Field of Search ................................. 424/49–58; 514/900–902

[56] References Cited

U.S. PATENT DOCUMENTS

| | | | |
|---|---|---|---|
| 4,552,899 | 11/1985 | Sunshine | 514/568 |
| 4,619,934 | 10/1986 | Sunshine et al. | 514/227 |
| 4,722,938 | 2/1988 | Sunshine et al. | 514/479 |
| 4,738,966 | 4/1988 | Sunshine et al. | 514/227 |
| 4,749,697 | 6/1988 | Sunshine et al. | 514/226.5 |
| 4,749,711 | 6/1988 | Sunshine et al. | 514/226.5 |
| 4,749,720 | 6/1988 | Sunshine et al. | 514/567 |
| 4,749,721 | 6/1988 | Sunshine et al. | 514/567 |
| 4,749,722 | 6/1988 | Sunshine et al. | 514/567 |
| 4,749,723 | 6/1988 | Sunshine et al. | 514/567 |
| 4,780,463 | 10/1988 | Sunshine et al. | 514/226.5 |
| 4,783,465 | 11/1988 | Sunshine et al. | 514/235 |

OTHER PUBLICATIONS

CA. 106:72920e (1986) Belsole, U.S. Pat. No. 4,602,040.
CA. 109:11746t (1988) Bani, E.P.O. 252033.
Kempf et al., "Comparison of Meclofenamate Sodium with Buffered Aspirin and Placebo for the Relief of Postoperative Dental Pain", *Clinical Therapeutics*, vol. 9, No. 6, 1987, 594–601.
Vogel et al., "The Effects of a Topically-Active Non-Steroidal Anti-Inflammatory Drug on Ligature-Induced Periodontal Disease in the Squirrel Monkey", *J. Clin. Periodontal* 1986; 13; 139–144.
Jeffcoat et al., "Treating Periodontal Disease", *Dentistry*, Apr. 1986, 29–32.
Lerner and Hanstrom, "Human Gingival Fibroblasts Secrete Non-Dialyzable Prostanoid-Independent Products Which Stimulate Bone Resorption in Vitro", *J. Periodontal Res.* 22(4); 284–28.
Lerner, et al., "Brandykinin, A New Potential Mediator of Inflammation-Induced Bone Resorption", *Arthritis and Rheumatism*, vol. 30, No. 5, May 1987.

*Primary Examiner*—Shep K. Rose
*Attorney, Agent, or Firm*—Charles A. Gaglia, Jr.; Carl W. Battle

[57] ABSTRACT

2-(2,6-Dichloro-3-methylphenylamino)benzoic acid and its physiologically acceptable salts are effective in inhibiting the conversion of gingivitis to periodontitis and thus useful in treating destructive periodontal disease. The therapeutic agent can be applied directly to the gingival tissue in a topically administerable pharmaceutical composition or can be introduced and released in the buccal cavity for contact with the gingival tissue through the fluid motion present in the mouth.

3 Claims, No Drawings

METHOD OF AND COMPOSITIONS FOR TREATING DESTRUCTIVE PERIODONTAL DISEASE

The present invention pertains to a method of treating destructive periodontal diseases in a warm blooded animal and to compositions useful in the practice of that method.

BACKGROUND OF THE INVENTION

The term periodontal diseases relates to conditions in which the gingiva and underlying alverolar bone are attacked. The condition exists in a number of species of warm blooded animals such as humans and canines, and appears at least initially to involve an inflammatory and immunological response to the stimuli of bacterial plaque. Clinically the advance of the disease involves conversion of chronic gingivitis, involving primarily inflammation of the gingiva, to chronic destructive periodontitis, in which resorption of the alveolar bone, increased mobility of the teeth, and in advance stages, loss of teeth are observed.

Current therapy involves mechanical and chemical control of the flora, coupled with establishing good oral hygiene. Because of the initial inflammatory aspect of the disease, a number of workers have investigated the use of anti-inflammatory agents. Various steroidal agents such as hydrocortisone and prednisolone thus have been reported to be beneficial in reducing the inflammation of the gingiva when administered systemically or topically. Some nonsteroidal anti-inflammatory agents such as aspirin and indomethacin also have been reported to be effective systemically whereas others such as sulindac have reported to be ineffective. Belgian Patent No. 900,481 reports that ibuprofen and flurbiprofen are effective in preventing or inhibiting alveolar bone resorption when administered orally or topically at low, non-anti-inflammatory dosage levels.

DETAILED DESCRIPTION

The present invention is based on the discovery that 2-(2,6-dichloro-3-methylphenylamino)benzoic acid and its physiologically acceptable salts are effective in inhibiting the conversion of gingivitis to periodontitis and thus useful in treating destructive periodontal disease in warm blooded animals. 2-(2,6-Dichloro-3-methylphenylamino)benzoic acid, or meclofenamic acid, is a known nonsteroidal anti-inflammatory agent, but its anti-inflammatory activity does not appear to be responsible for its ability to alter the progression of gingivitis to periodontitis since such action is not accompanied by a reduction in clinically detectable inflammation. Nor does it appear that the therapy substantially alters the subgingival microbiota.

The present method comprises bringing into contact with the gingival tissue of the animal an effective amount of 2-(2,6-dichloro-3-methylphenylamino)benzoic acid, or a physiologically acceptable salt thereof. This is accomplished through use of a composition containing an effective amount of 2-(2,6-dichloro-3-methylphenylamino)benzoic acid, or a physiologically acceptable salt thereof, in combination with a physiologically acceptable carrier operable to deliver the therapeutic agent in the environs of or to the animal's gingival tissue for topical contact therewith. Thus the therapeutic agent can be applied directly to the gingival tissue in a topically administerable pharmaceutical composition or can be introduced and released in the buccal cavity and then allowed to contact the gingival tissue through the fluid motion present in the mouth.

It will be appreciated that while the principal route of application is topical, the therapeutic effect may involve a systemic response or component upon absorption and thus the use of other routes producing a substantially equivalent systemic response are possible.

Suitable carriers for topical application include aqueous vehicles, gel bases, ointments, pastes, dental adhesives, and the like.

Carriers for compositions from which the therapeutic agent can be introduced and released in the buccal cavity for contact with the gingival tissue include dissolvable tablets, troches, chewing gums, toothpaste formulations, lozenges, and comestibles. In each of these, the therapeutic agent is released from the composition in the course of chewing or sucking and allowed to pass over the gingival tissue over a period of time. Comestibles include any compatible beverage or foodstuff which is retained in the buccal cavity sufficiently long to release the active ingredient. The latter formulations, particularly those which must be chewed, are useful with non-human patients such as canines in which repeated topical application of formulations may be difficult or inconvenient.

It is often useful for formulation purposes to employ a salt of 2-(2,6-dichloro-3-methylphenylamino)benzoic acid and a base such as the alkali metals, alkaline earth metals, non-toxic metals, ammonium, and mono-, di- and trisubstituted amines. Typical of these are the sodium, potassium, lithium, calcium, magnesium, aluminum, zinc, ammonium, trimethylammonium, triethanolammonium, t-butylammonium, pyridinium, and substituted pyridinium salts.

The amount of therapeutic agent applied generally will be in the range of from about 4 mg to about 400 mg. Compositions thus will be formulated so that the therapeutic agent will be present in a concentration of from about 0.09% to about 15% by weight of the composition. Preferably the concentration is from about 0.5% to about 10% and most preferably from about 1% to about 8%.

The therapeutic effect can be conveniently observed in laboratory periodontitis models, of which the following is typical.

Three groups of eighteen adult female cynomolgus monkeys (a total of 54) were treated under blind conditions. All animals previously had been placed on a soft chow diet during an eight week quarantine period and then given a complete oral examination. All animals had existing gingivitis, as is normally observed in this test animal. A formulation of either 5% meclofenamic acid or 8% ibuprofen, or a placebo formulation was applied topically to the gums of a group five times a week for a four week preinduction period. Conversion of gingivitis to periodontitis then was induced by typing a 3-0 silk suture at the cement-enamel junction of the mandibular second premolars and second molars according to the method of Kornman et al., *J. Periodon Res.* 16: 363 (1981) and treatment was continued five times a week for an additional sixteen weeks.

During the study, supragingival plaque was scored by the Plaque Index and gingival bleeding after probing was scored by the Gingival Index, both described by Silness and Loe, *Acta Odontol. Scand.* 21: 533 (1963). Pocket depth was measured from the gingival margin to the base of the sulcus by means of a Michigan "0"

probe. Changes in bone density of the marginal bone were monitored by standardized serial radiographs and analyzed by the method of Bragger et al., *J. Clin. Periodon.* 15: 29 (1988). Polymorphonuclear leukocyte chemotaxis was monitored by a modification of the method of Golub et al., *Infect. Immun.* 37: 1013 (1982). Microbiological counts and cultures were monitored by conventional techniques.

The values as of the date of conversion of gingivitis to periodontitis were utilized as the baseline data. At this point, the control (placebo) group showed a statistically significantly higher gingival index, lower plaque index, and lower mean ranked count of polymorphonuclear (PMN) leukocytes. Differences in probe depths were not satistically significant.

TABLE I

| Group | Base-line Values[1] | | | |
|---|---|---|---|---|
| | G.I.[2] | P.I.[3] | P.D.[4] | PMN[5] |
| Control | 42.50* | 21.5* | 29.50 | 18.67* |
| Meclofenamic Acid | 16.75 | 68.50 | 49.25 | 52.83 |
| Ibuprofen | 12.17 | 41.58 | 32.83 | 40.17 |

[1]Clinical data and PMN counts expressed as means of ranked counts by index (or PMN count) and drug.
[2]G.I. = Gingival Index (Silness and Loe, supra).
[3]P.I. = Plaque Index (Silness and Loe, supra).
[4]P.D. = Probe Depth.
[5]PMN = Polymorphonuclear leukocytes (modification of Golub et al., supra).
*statistically significant by variance analysis.

When analyzed between weeks 6 to 10, no satistically significant difference was seen in gingival index, plaque index, PMN, or probe depths.

TABLE II

| Group | 6-10 Week Values | | | |
|---|---|---|---|---|
| | G.I. | P.I. | P.D. | PMN |
| Control | 54.33 | 38.42 | 54.00 | 31.50 |
| Meclofenamic Acid | 63.08 | 41.58 | 70.42 | 49.97 |
| Ibuprofen | 48.58 | 62.08 | 39.75 | 34.17 |

*statistically significant by variance analysis.

When analyzed between weeks 14-16, no satistically significant difference was seen in gingival index or plaque index. A statistically significant deeper probe depth and statistically significant higher PMN count was observed for meclofenamic acid, as compared with the control and ibuprofen.

TABLE III

| Group | 14-16 Week Values | | | |
|---|---|---|---|---|
| | G.I. | P.I. | P.D. | PMN |
| Control | 38.33 | 39.00 | 36.17 | 18.67 |
| Meclofenamic Acid | 53.08 | 52.08 | 70.42* | 59.50* |
| Ibuprofen | 56.42 | 52.75 | 34.92 | 21.17 |

At weeks 14-16, no statistically significant difference was seen in microscopic data.

TABLE IV

| Group | 14-16 Week Values[1] | | | |
|---|---|---|---|---|
| | Cocci | Filaments | Rods | Spirochetes |
| Control | 20.50 | 30.00 | 40.42 | 13.75 |
| Meclofenamic Acid | 7.25 | 25.50 | 41.08 | 21.92 |
| Ibuprofen | 20.17 | 25.50 | 30.25 | 25.17 |

[1]Data presented as ranked mean percentages of groups of organisms recognized by cellular morphology.

The foregoing clinical and microscopic observations do not reflect a significant change in the extreme gingivitis which is established in this model. The results of radiographic examination however demonstrate the ability of meclofenamic acid to intervene significantly in bone loss associated with the conversion of gingivitis to periodontitis, as can be seen from the following:

TABLE V

| Group | Mean Net Bone Density Loss | | | |
|---|---|---|---|---|
| | Weeks Post-ligation | | | |
| | 0 | 2 | 6 | 16 |
| Control | +0.42 | −1.03[1] | −2.46 | −1.14 |
| Meclofenamic Acid | +2.91 | −0.15 | +6.49 | +8.17 |
| Ibuprofen | +2.43 | −3.63 | +0.74 | +1.56 |

[1]Negative values reflect net loss of bone density; positive values reflect net gain in bone density.

The percentage of response in preventing a loss in bone density can be summarized as follows:

TABLE VI

| Group | Loss of Bone Density | | Net Loss of Bone Density[1] | |
|---|---|---|---|---|
| | Sites | Percent | Sites | Percent |
| Control | 18/18 | 100.0% | 15/18 | 83.3% |
| Meclofenamic Acid | 8/18 | 44.4% | 8/18 | 44.4% |
| Ibuprofen | 12/18 | 66.7% | 9/18 | 50.5% |

[1]Loss of bone density summed with any gains in bone density.

The following examples will serve to typify representative formulations but should not be construed as limitation on the scope of this invention, the scope being defined solely by the appended claims.

EXAMPLE 1

The following components are thoroughly blended to produce a topical gel formulation suitable for direct application to the gingival tissue:

| | Parts |
|---|---|
| PEG-6 Capric/caprylic Triglycerides | 59.5 |
| Polyethylene Glycol 6000 | 13.7 |
| Alcohol U.S.P. | 21.8 |
| Meclofenamic Acid | 5.0 |

EXAMPLE 2

The following ingredients are blended to produce a dentifrice:

| | Parts |
|---|---|
| Deionized Water | 27.758 |
| Glycerine | 25.0 |
| Silica (Abrasive) | 40.0 |
| Sodium Lauryl Sulfate | 1.2 |
| Flavor | 1.0 |
| Xanthan Gum | 1.0 |
| Sodium Benzoate | 0.5 |
| Sodium Saccharin | 0.3 |
| Sodium Fluoride | 0.242 |
| Titanium Dioxide | 0.5 |
| Meclofenamic Acid | 2.5 |

Other abrasives such as dicalcium phosphate can be substituted in whole or part for the silica. Upon normal use, the dentifrice will release the meclofenamic acid in the buccal cavity for indirect application to the gingival tissue.

EXAMPLE 3

A mouthwash composition which upon use introduces meclofenamic acid in the buccal cavity for indirect application to the gingival tissue can be prepared as follows:

|  | Parts |
| --- | --- |
| Alcohol U.S.P. | 15.0 |
| Sorbitol | 20.0 |
| Pluronic F-127 | 1.0 |
| Flavor | 0.4 |
| Sodium Saccharin | 0.03 |
| Sodium Fluoride | 0.05 |
| Meclofenamic Acid, Sodium Salt | 0.50 |
| Deionized Water q.s. | 100.00 |

EXAMPLE 4

A chewing gum composition which upon use introduces meclofenamic acid in the buccal cavity for indirect application to the gingival tissue can be prepared as follows:

|  | Parts |
| --- | --- |
| Gum Base | 10 to 50 |
| Binder | 3 to 10 |
| Filler (sorbitol, mannitol, or combination thereof) | 5 to 80 |
| Artificial Sweetener (saccharin, aspartame, acesulfame K, or sodium cyclamate, etc.) | 0.1 to 5 |
| Flavor | 0.1 to 5 |
| Meclofenamic Acid | 0.5 to 5 |

EXAMPLE 5

Lozenges can be prepared according to the following composition:

|  | Parts |
| --- | --- |
| Sugar | 75 to 90 |
| Corn Syrup | 1 to 20 |
| Meclofenamic Acid | 0.5 to 5.0 |

What is claimed is:

1. In the method of treating destructive periodontal disease in a warm blooded animal which comprises bringing into contact with the gingival tissue of said animal a non-steroidal anti-inflammatory agent, the improvement as compared to ibuprofen, with significant reduction of bone loss associated with the conversion of gingivitis to periodontitus which consists of the steps of contacting said gingival tissues with an effective amount of 2-(2,6-dichloro-3-methylphenylamino)benzoic acid, or a physiologically acceptable salt thereof.

2. The method according to claim 1 wherein 2-(2,6-dichloro-3-methylphenylamino)benzoic acid, or a physiologically acceptable salt thereof, is applied directly to the gingival tissue in a topically administerable pharmaceutical composition.

3. The method according to claim 1 wherein 2-(2,6-dichlor-3-methylphenylamino)benzoic acid, or a physiologically acceptable salt thereof, is introduced and released in the buccal cavity and allowed to contact the gingival tissue thereof.

* * * * *